US00PP11976P2

(12) United States Plant Patent
Dubin

(10) Patent No.: US PP11,976 P2
(45) Date of Patent: Jul. 3, 2001

(54) HIBISCUS PLANT NAMED 'HOOSIERS'

(76) Inventor: Dale Dubin, 1385 Sautern Dr., Fort Myers, FL (US) 33919

( * ) Notice: Subject to any disclaimer, the term of this patent is extended or adjusted under 35 U.S.C. 154(b) by 0 days.

(21) Appl. No.: 09/396,485

(22) Filed: Sep. 15, 1999

(51) Int. Cl.[7] ..... A01H 5/00
(52) U.S. Cl. ..... Plt./257
(58) Field of Search ..... Plt./257

(56) References Cited

U.S. PATENT DOCUMENTS

P.P. 2,761 * 8/1967 Gast ..... Plt./257

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Hibiscus plant named 'Hoosiers', characterized by its upright and somewhat spreading plant habit; vigorous growth habit; shiny dark green leaves; large and unique bi-colored flowers with pure white center surrounded by dark red margin; and red and white vertically striped styles.

1 Drawing Sheet

BACKGROUND OF THE INVENTION

The present invention relates to a new and distinct cultivar of Hibiscus, botanically know as *Hibiscus rosa-sinensis* and hereinafter referred to by the cultivar name 'Hoosiers'.

The new Hibiscus is a product of a planned breeding program conducted by the Inventor in Fort Myers, Fla. The objective of the program was to create new Hibiscus selections with red and white bi-colored flowers.

The new Hibiscus originated from a cross made by the Inventor in Fort Myers, Fla., of the *Hibiscus rosa-sinensis* cultivar 'Starfish', not patented, as the female, or seed, parent with the *Hibiscus rosa-sinensis* cultivar 'Coconut Ice', not patented, as the male, or pollen, parent. The cultivar 'Hoosiers' was discovered and selected by the Inventor as a flowering plant within the progeny of the stated cross in a controlled environment in Fort Myers, Fla.

Plants of the new Hibiscus have white and dark red bi-colored flowers, whereas plants of the cultivar 'Starfish' have yellow and red-orange bi-colored flowers and plants of the cultivar 'Coconut Ice' have light pink-colored flowers.

Asexual reproduction of the new Hibiscus by terminal cuttings taken in a controlled environment in Fort Myers, Fla., has shown that the unique features of this new Hibiscus are stable and reproduced true to type in successive generations.

SUMMARY OF THE INVENTION

The cultivar 'Hoosiers' has not been observed under all possible environmental conditions. The phenotype may vary somwehat with variations in environment such as temperature, light intensity, nutrition and water status without, however, any variance in genotype.

The following traits have been repeatedly observed and are determined to be the unique characteristics of 'Hoosiers'. These characteristics in combination distinguish 'Hoosiers' as a new and distinct cultivar:

1. Upright and somewhat spreading plant habit.
2. Vigorous growth habit.
3. Shiny dark green leaves.

4. Large and unqiue bi-colored flowers with pure white center surrounded by dark red margin.
5. Style base with red and white vertical stripes.

Plants of the new Hibiscus can be compared to plants of the cultivar 'Restless Heart', not patented. However, in sidy-by-side comparisons conducted in Fort Myers, Fla., plants of the new Hibiscus differ from plants of the cultivar 'Restless Heart' in the following characteristics:

1. Flowers of plants of the new Hibiscus have a larger white central area and darker red margin color than flowers of plants of the cultivar 'Restless Heart'.
2. Plants of the new Hibiscus have red and white striped styles whereas plants of the cultivar 'Restless Heart' have white styles.

Plants of the new Hibiscus can be compared to plants of the cultivar 'Red 'N White', not patented. However, in side-by-side comparisons conducted in Fort Myers, Fla., plants of the new Hibiscus differ from plants of the cultivar 'Red 'N White' in the following characteristics:

1. Flowers of plants of the new Hibiscus have a larger white central area and darker red margin color than flowers of plants of the cultivar 'Red 'N White'.
2. Plants of the new Hibiscus have red and white striped styles whereas plants of the cultivar 'Red 'N White' have white styles.
3. Flowers of plants of the new Hibiscus have distinct red and white areas whereas flowers of plants of the cultivar 'Red 'N White' have white spots scattered throughout the red area.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type. Colors in the photographs may differ slightly from the color values cited in the detailed botanical description which accurately describe the actual colors of the new Hibiscus.

The photograph at the top of the sheet comprises a side perspective view of a typical plant of 'Hoosiers'.

The photograph at the bottom of the sheet comprises a close-up view of a typical flower of 'Hoosiers'.

DETAILED BOTANICAL DESCRIPTION

The following observations, measurements and values describe plants grown in Fort Myers, Fla., during the late spring, under polypropylene shadecloth providing a 40 percent light reduction, and conditions which closely approximate commercial production. Plants described were about one-year old.

In the description, color references are made to The Royal Horticultural Society Colour Chart except where general terms of ordinary dictionary significance are used.

Botanical classification: *Hibiscus rosa-sinensis* cultivar 'Hoosiers'.

Parentage:

*Female or seed parent.*—*Hibiscus rosa-sinensis* cultivar 'Starfish', not patented.

*Male or pollen parent.*—*Hibiscus rosa-sinensis* cultivar 'Coconut Ice', not patented.

Propagation:

*Type.*—By cuttings.

*Time to initiate roots, summer.*—About 14 days at temperatures of about 24 to 29° C.

*Time to initiate roots, winter.*—About 14 days at temperatures of 10 to 24° C.

*Time to develop roots, summer.*—About 42 days at temperatures of about 27° C.

*Time to develop roots, winter.*—About 42 to 56 days at temperatures of about 18° C.

*Root description.*—Fine to medium; fibrous, freely branching.

Plant description:

*Plant form and growth habit.*—Perennial, evergreen shrub. Mostly upright and somewhat spreading.

*Branching habit.*—Freely branching, usually about five to ten lateral branches develop after pinching.

*Plant height, soil level to top of flowers.*—About 1.52 meters; plants grow about 15 cm per month.

*Plant diameter, area of spread.*—About 1.37 meters.

*Vigor.*—Vigorous.

*Lateral branch description.*—Length: About 91 cm. Diameter: About 7.5 mm. Internode length: About 6 cm. Strength: Strong. Texture: Smooth, glabrous. Color: 143B.

Foliage description:

*Arrangement.*—Alternate, single; symmetrical.

*Quantity per lateral branch.*—About 3 to 15.

*Length.*—About 9 cm.

*Width.*—About 9 cm.

*Shape.*—Cordate.

*Apex.*—Acuminate.

*Base.*—Cordate.

*Margin.*—Serrate to entire.

*Texture.*—Glabrous, shiny.

*Color.*—Young foliage, upper surface: 147B. Young foliage, lower surface: 146B. Mature foliage, upper surface: 147A. Mature foliage, lower surface: 146A.

*Petiole.*—Length: About 4.5 cm. Diameter: About 2 mm. Color: 143B.

Flower description:

*Natural flowering season.*—Typically year-round under subtropical and tropical conditions.

*Flower arrangement.*—Flowers arranged singly at terminal leaf axils. Flower face mostly upright to slightly outward.

*Flower appearance.*—Roughly rounded; large pure white center surrounded by distinct dark red margin. Flowers are open for about one day before closing. Flowers persistent.

*Fragrance.*—None detected.

*Flower diameter.*—About 10 cm.

*Flower bud* (*just before showing color*).—Rate of opening: About one or three days depending on temperature. Length: About 4.5 cm. Diameter: About 2 cm. Shape: Oval, fusiform. Color: 12C.

*Petals.*—Arrangement: Corolla consists of five flat petals that overlap. Length: About 7 cm. Width: About 5.5 cm. Shape: Roughly spatulate with rounded apex. Margin: Entire, but slightly ruffled. Texture: Smooth. Color: Upper surface, when opening and fully opened: Center, white, 155C, surrounded by dark red, 45B. White area extends to about one-half the length of the petal. Flower color does not fade with subsequent development. Lower surface, when opening and fully opened: 12C.

*Sepals.*—Appearance: Five sepals fused into a star-shaped calyx. Shape: Cordate. Apex: Acuminate. Margin: Entire. Color, both surfaces: 143A.

*Peduncles.*—Length: About 2.5 cm. Angle: About 45° from vertical. Strength: Strong, flexible. Diameter: About 2.5 mm. Color: Close to 146A.

*Reproductive organs.*—Androecium: Anther length: About 2 mm. Anther color: 14C. Amount of pollen: Moderate. Pollen color: 14B. Gynoecium: Pistil quantity: One. Pistil length: About 4.25 cm. Style length: About 3.75 cm. Style color: White with five vertical red, 45B, stripes at base. Stigma shape: Oval. Stigma color: 23B. Ovary color: White.

Disease resistance: Resistance to known Hibiscus diseases has not been observed on plants grown under conditions approximating commercial practices.

Seed production:

*Quantity.*—About 12 seeds per seed capsule.

*Length.*—About 3 mm.

*Diameter.*—About 2.5 mm.

*Color.*—200A.

It is claimed:

1. A new and distinct Hibiscus plant named 'Hoosiers', as illustrated and described.

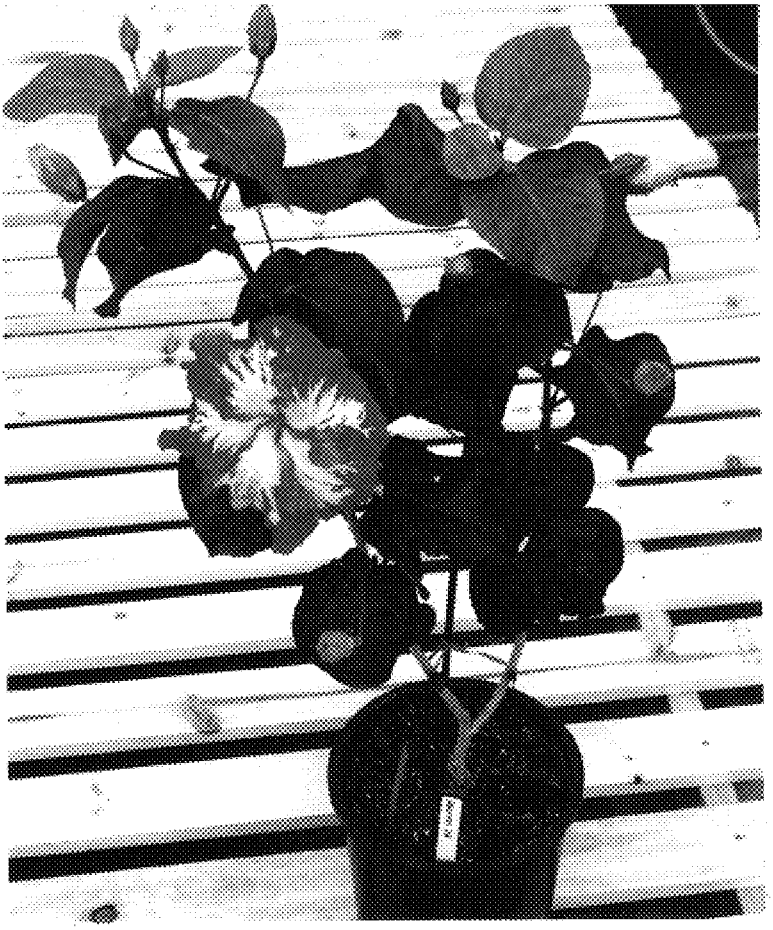
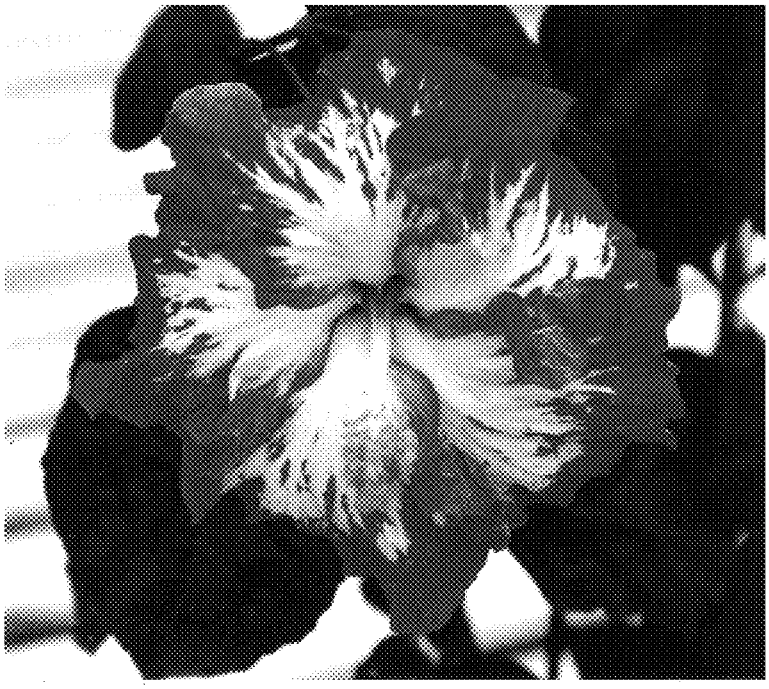

* * * * *